United States Patent

Ansmann et al.

[11] Patent Number: 5,939,081
[45] Date of Patent: Aug. 17, 1999

[54] ESTERS OF ALKYL AND/OR ALKENYL OLIGOGLYCOSIDES WITH FATTY ACIDS

[75] Inventors: Achim Ansmann, Erkrath; Rolf Kawa, Monheim; Annette Kreisig, Duesseldorf, all of Germany; Norman Milstein, Montgomery, Ohio

[73] Assignee: Henkel Kommanditgesellschaft auf Aktien, Duesseldorf, Germany

[21] Appl. No.: 08/806,878

[22] Filed: Feb. 26, 1997

Related U.S. Application Data

[60] Provisional application No. 60/012,338, Feb. 27, 1996.

[51] Int. Cl.⁶ .................. A61K 7/00; A61K 7/48
[52] U.S. Cl. .................. 424/401; 514/937; 514/938; 536/115; 536/4.1
[58] Field of Search .................. 424/401, 59, 70.31, 424/70.24; 514/23, 24, 784, 785, 937, 938, 844, 25; 536/18.4, 18.5, 18.6, 115, 4.1

[56] References Cited

U.S. PATENT DOCUMENTS

| | | | |
|---|---|---|---|
| 3,547,828 | 12/1970 | Mansfield et al. | 252/351 |
| 3,707,535 | 12/1972 | Lew | 260/210 R |
| 3,839,318 | 10/1974 | Mansfield | 260/210 R |
| 4,349,669 | 9/1982 | Klahr et al. | 536/127 |
| 4,364,837 | 12/1982 | Pader | 252/173 |
| 5,109,127 | 4/1992 | Sekiguchi et al. | 536/115 |
| 5,374,716 | 12/1994 | Biermann et al. | 536/18.6 |
| 5,431,840 | 7/1995 | Soldanski et al. | 252/174.17 |
| 5,576,425 | 11/1996 | Hill et al. | 536/18.6 |
| 5,656,200 | 8/1997 | Boettcher et al. | 252/307 |

FOREIGN PATENT DOCUMENTS

| | | |
|---|---|---|
| 0077167 | 4/1983 | European Pat. Off. . |
| 0301298 | 2/1989 | European Pat. Off. . |
| 0334498 | 9/1989 | European Pat. Off. . |
| 1165574 | 3/1964 | Germany . |
| 1943689 | 3/1970 | Germany . |
| 2036472 | 2/1971 | Germany . |
| 2360367 | 6/1974 | Germany . |
| 3001064 | 7/1981 | Germany . |
| 2024051 | 5/1986 | Germany . |
| 4022540 | 1/1992 | Germany . |
| WO90/03977 | 4/1990 | WIPO . |

OTHER PUBLICATIONS

C. Cabeza, et al., "Influencia sobre la consistencia de cremas O/W en dependencia de su elaboración y formulación", SÖFW–Journal, 120, Jahrgang, Apr. 1994, pp. 162–176.
"Kosmetische Färbemittel", Farbstoffkommission der Deutschen Forschungsgemeinschaft, Verlag Chemie, Weinheim, 1984, pp. 81–106.

*Primary Examiner*—Thurman K. Page
*Assistant Examiner*—Lakshmi Channavajjala
*Attorney, Agent, or Firm*—Wayne C. Jaeschke; John E. Drach; Steven J. Trzaska

[57] ABSTRACT

A process for thickening a water-in-oil and oil-in-water emulsion involving adding to the emulsion a thickening agent consisting of an alkyl or alkenyl oligoglucoside ester formed by esterifying an alkyl or alkenyl oligoglycoside corresponding to formula I:

$$R^1O\text{—}[G]_p \qquad (I)$$

wherein $R^1$ is an alkyl or alkenyl oligoglucoside containing from about 4 to about 22 carbon atoms, G is a sugar unit containing from 5 to 6 carbon atoms, and p is a number having a value of from 1 to about 10, with a fatty acid corresponding to formula II:

$$R^2CO\text{—}OH \qquad (II)$$

wherein $R^2CO$ is an aliphatic acyl radical containing from about 6 to about 22 carbon atoms, and up to about 3 double bonds.

14 Claims, No Drawings

ESTERS OF ALKYL AND/OR ALKENYL OLIGOGLYCOSIDES WITH FATTY ACIDS

BENEFIT OF EARLIER FILING DATE UNDER 37 CFR 1.78(A)(4)

This application claims the benefit of earlier filed and provisional application Ser. No. 60/012,338 filed on Feb. 27, 1996.

BACKGROUND OF THE INVENTION

1. Field of the Invention

This invention relates to the use of special glycoside esters as emulsifiers for the production of cosmetic and/or pharmaceutical formulations.

2. Description of the Related Art

The production of cosmetic and pharmaceutical formulations, for example creams, lotions and salves, generally entails the use of aqueous and oily constituents which are not readily miscible with one another. It is only the addition of suitable emulsifiers which enables stable emulsions of the water-in-oil or oil-in-water type to be formed. The emulsifiers may be selected from a range of substances which are capable of reducing interfacial tension. Typical examples are fatty acid partial glycerides, polyglycerol esters, alkyl polyglucosides, fatty alcohols and the like. In many cases, the production of stable emulsions is dependent upon the careful choice of a suitable emulsifier system even though modern formulation techniques can be helpful in this regard (cf. for example C. Cabeza et al. in SÖFW-Journal 120, 162 (1994) and A. Ansmann et al. ibid 120, 158).

Nevertheless, the product developer is often left with no alternative but to select the appropriate emulsifier(s) from a range of suitable emulsifiers for a specific formulation. If different emulsions are to be produced, this means that a number of emulsifiers have to be kept available which involves expensive and, hence, unwanted storage.

Another problem is that, although certain emulsifiers are capable of reliably ensuring emulsion formation, they do not have a thickening effect, i.e. additional viscosity-increasing substances have to be added where it is desired to build up a high viscosity (for example in a cream). Alternatively, natural waxes, for example beeswax, may also be used although they are expensive and are difficult to process.

Accordingly, the problem addressed by the present invention was to provide new "all-round" emulsifiers which would make it possible to produce both o/w and w/o emulsions and which, at the same time, would build up a satisfactorily high viscosity in the emulsions so that it would no longer be necessary, for example, to use expensive natural waxes.

SUMMARY OP THE INVENTION

The surprising discovery has been made that a cosmetic and/or pharmaceutical emulsion can be thickened by adding to the emulsion a thickening-effective amount of an ester of an alkyl and/or oligoglycoside and a fatty acid having from about 6 to about 22 carbon atoms.

DESCRIPTION OF THE INVENTION

Other than in the claims and in the operating examples, or where otherwise indicated, all numbers expressing quantities of ingredients or reaction conditions used herein are to be understood as modified in all instances by the term "about".

The present invention relates to the use of esters of alkyl and/or alkenyl oligoglycosides with fatty acids containing 6 to 22 carbon atoms as emulsifiers for the production of cosmetic and/or pharmaceutical formulations.

It has surprisingly been found that glucosides are capable of stabilizing both o/w and w/o emulsions. In the production of w/o emulsions in particular, the use of the glycoside esters makes it possible to establish a viscosity and stability which otherwise could only be achieved using the very expensive and difficult-to-process beeswax. The ability of the glycoside esters to emulsify totally different systems and, at the same time, to build up a high viscosity makes it possible inter alia to reduce the number of starting materials required for the formulation of cosmetic and pharmaceutical emulsions and hence to save storage costs and control costs for incoming goods. The invention includes the observation that the use of fatty alcohols and/or partial glycerides as co-emulsifiers is of advantage for building up particularly high viscosities.

Alkyl and/or alkenyl oligoglycoside fatty acid esters

Esters of alkyl and/or alkenyl oligoglycosides and fatty acids, which are referred to hereinafter in brief as "glycoside esters", are known from the prior art, examples of which include U.S. Pat. No. 5,109,127 and U.S. Pat. No. 5,431,840, the entire contents which are incorporated herein by reference. Although they are normally methyl glucoside esters, the production of the esters with higher fatty acids is also carried out by methods known per se, i.e. by alkali-catalyzed esterification of the starting materials which are described in more detail hereinafter. Technical mixtures of products with various degrees of substitution are normally formed in the esterification process. However, monoesters and, in particular, diesters or technical mixtures thereof are preferably used as emulsifiers.

Alkyl and/or alkenyl oligoglycosides

Alkyl and alkenyl oligoglycosides are known nonionic surfactants corresponding to formula (I):

$$R^1O\text{---}[G]_p \tag{I}$$

in which $R^1$ is an alkyl and/or alkenyl radical containing 4 to 22 carbon atoms, G is a sugar unit containing 5 or 6 carbon atoms and p is a number of 1 to 10. They may be obtained by the relevant methods of preparative organic chemistry. EP-A1 0 301 298 and WO 90/03977 are cited as representative of the extensive literature available on the subject.

The alkyl and/or alkenyl oligoglycosides may be derived from aldoses or ketoses containing 5 or 6 carbon atoms, preferably glucose. Accordingly, the preferred alkyl and/or alkenyl oligoglycosides are alkyl and/or alkenyl oligoglucosides.

The index p in general formula (I) indicates the degree of oligomerization (DP degree), i.e. the distribution of mono- and oligoglycosides, and is a number of 1 to 10. Whereas p in a given compound must always be an integer and, above all, may assume a value of 1 to 6, the value p for a certain alkyl oligoglycoside is an analytically determined calculated quantity which is generally a broken number. Alkyl and/or alkenyl oligoglycosides having an average degree of oligomerization p of 1.1 to 3.0 are preferably used. Alkyl and/or alkenyl oligoglycosides having a degree of oligomerization of less than 1.7 and, more particularly, between 1.2 and 1.4 are preferred from the applicational point of view.

The alkyl or alkenyl radical $R^1$ may be derived from primary alcohols containing 4 to 11 and preferably 8 to 10 carbon atoms. Typical examples are butanol, caproic alcohol, caprylic alcohol, capric alcohol and undecyl alcohol and the technical mixtures thereof obtained, for example, in the hydrogenation of technical fatty acid methyl esters or in the hydrogenation of aldehydes from Roelen's oxosynthesis. Alkyl oligoglucosides having a chain length of $C_8$ to $C_{10}$ (DP=1 to 3), which are obtained as first runnings in the separation of technical $C_{8-18}$ coconut oil fatty alcohol by distillation and which may contain less than 6% by weight of $C_{12}$ alcohol as an impurity, and also alkyl oligoglucosides based on technical $C_{9-11}$ oxoalcohols (DP=1 to 3) are preferred.

In addition, the alkyl or alkenyl radical $R^1$ may also be derived from primary alcohols containing 12 to 22 and preferably 12 to 14 carbon atoms. Typical examples are lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and technical mixtures thereof which may be obtained as described above. Alkyl oligoglucosides based on hydrogenated $C_{12-14}$ coconut oil fatty alcohol having a DP of 1 to 3 are preferred.

Fatty acids

Fatty acids in the context of the present invention are understood to be aliphatic carboxylic acids corresponding to formula (II):

$$R^2CO\text{---}OH \qquad (II)$$

in which $R^2CO$ is an aliphatic, linear or branched acyl radical containing 6 to 22 carbon atoms and 0 and/or 1, 2 or 3 double bonds. Typical examples are caproic acid, caprylic acid, 2-ethylhexanoic acid, capric acid, lauric acid, isotridecanoic acid, myristic acid, palmitic acid palmitoleic acid, stearic acid, isostearic acid, oleic acid, elaidic acid, petroselic acid, linoleic acid, linolenic acid, elaeostearic acid, arachic acid, gadoleic acid, behenic acid and erucic acid and the technical mixtures thereof obtained, for example, in the pressure hydrolysis of natural fats and oils, in the reduction of aldehydes from Roelen's oxosynthesis or in the dimerization of unsaturated fatty acids.

Overall preference is attributed to monoesters and diesters of alkyl oligoglucosides containing 8 to 18 carbon atoms in the alkyl radical and fatty acids containing 16 to 18 carbon atoms. It is of particular advantage to use cocoalkyl oligoglucoside monopalmitate or dipalmitate, cocoalkyl oligoglucoside monostearate or distearate, coco-oligoglucoside monoisostearate or diisostearate and/or coco-oligoglucoside mono-oleate or dioleate. The quantity used may be from 1 to 10% by weight and is preferably from 2 to 8% by weight, based on the emulsions.

Commercial Applications

With the aid of the glycoside esters to be used in accordance with the invention, it is possible to produce both o/w and w/o emulsions which may be used for a range of cosmetic and/or pharmaceutical applications. Typical examples are day creams, night creams, care creams, nourishing cream, body lotions, emollients and the like which may contain as further auxiliaries and additives: oils, co-emulsifiers, superfatting agents, fats, waxes, stabilizers, biogenic agents, preservatives, dyes and fragrances.

Suitable oils are, for example, Guerbet alcohols based on fatty alcohols containing 6 to 18 and preferably 8 to 10 carbon atoms, esters of linear $C_{6-20}$ fatty acids with linear $C_{6-20}$ fatty alcohols, esters of branched $C_{6-13}$ carboxylic acids with linear $C_{6-20}$ fatty alcohols, esters of linear $C_{6-18}$ fatty acids with branched alcohols, more particularly 2-ethyl hexanol, esters of linear and/or branched fatty acids with polyhydric alcohols (for example dimer diol or trimer diol) and/or Guerbet alcohols, triglycerides based on $C_{6-10}$ fatty acids, vegetable oils, branched primary alcohols, substituted cyclohexanes, Guerbet carbonates, dialkyl ethers and/or aliphatic or naphthenic hydrocarbons.

Suitable co-emulsifiers are nonionic, ampholytic and/or zwitterionic interfacially active compounds which are distinguished by a lipophilic, preferably linear, alkyl or alkenyl group and at least one hydrophilic group. This hydrophilic group may be both an ionic group and a nonionic group.

Nonionic emulsifiers contain a polyol group, a polyalkylene glycol ether group or a combination of polyol and polyglycol ether groups, for example, as the hydrophilic group. Preferred formulations are those containing nonionic surfactants from at least one of the following groups as o/w emulsifiers: (a1) adducts of 2 to 30 moles of ethylene oxide and/or 0 to 5 moles of propylene oxide with linear fatty alcohols containing 8 to 22 carbon atoms, with fatty acids containing 12 to 22 carbon atoms and with alkylphenols containing 8 to 15 carbon atoms in the alkyl group; (a2) $C_{12-18}$ fatty acid monoesters and diesters of adducts of 1 to 30 moles of ethylene oxide with glycerol; (a3) glycerol monoesters and diesters and sorbitan monoesters and diesters of saturated and unsaturated fatty acids containing 6 to 22 carbon atoms and ethylene oxide adducts thereof; (a4) alkyl monoglycosides and oligoglycosides containing 8 to 22 carbon atoms in the alkyl radical and ethoxylated analogs thereof and (a5) adducts of 15 to 60 moles of ethylene oxide with castor oil and/or hydrogenated castor oil; (a6) polyol esters and, in particular, polyglycerol esters such as, for example, polyglycerol polyricinoleate or polyglycerol poly-12-hydroxystearate. Mixtures of compounds from several of these classes are also suitable. The addition products of ethylene oxide and/or propylene oxide with fatty alcohols, fatty acids, alkylphenols, glycerol monoesters and diesters and sorbitan monoesters and diesters of fatty acids or with castor oil are known commercially available products. They are homolog mixtures of which the average degree of alkoxylation corresponds to the ratio between the quantities of ethylene oxide and/or propylene oxide and substrate with which the addition reaction is carried out. $C_{12-18}$ fatty acid monoesters and diesters of adducts of ethylene oxide with glycerol are known as refatting agents for cosmetic formulations from DE-PS 20 24 051. $C_{8-18}$ alkyl monoglycosides and oligoglycosides, their production and their use as surfactants are known, for example from U.S. Pat. No. 3,839,318, U.S. Pat. No. 3,707,535, U.S. Pat. No. 3,547,828, DE-OS 19 43 689, DE-OS20 36 472 and DE-A1 30 01 064 and from EP-A 0 077 167. They are produced in particular by reaction of glucose or oligosaccharides with primary alcohols containing 8 to 18 carbon atoms. So far as the glycoside unit is concerned, both monoglycosides in which a cyclic sugar unit is attached to the fatty alcohol by a glycoside bond and oligomeric glycosides with a degree of oligomerization of preferably up to about 8 are suitable. The degree of oligomerization is a statistical mean value based on a homolog distribution typical of such technical products. Zwitterionic surfactants may also be used as emulsifiers. Zwitterionic surfactants are surfactants which contain at least one quaternary ammonium group and at least one carboxylate group and one sulfonate group in the molecule. Particularly suitable zwitterionic surfactants are the so-called betaines, such as the N-alkyl-N,N-dimethylammonium glycinates, for example cocoalkyl dimethylammonium glycinate, N-acylaminopropyl-N,N-dimethylammonium glycinates, for example cocoacyl aminopropyl dimethylammonium glycinate, and 2-alkyl-3-carboxymethyl-3-hydroxyethyl imidazolines containing 8 to 18 carbon atoms in the alkyl or acyl group and cocoacylaminoethylhydroxyethyl carboxymethyl glycinate. The fatty acid amide derivative known under the CTFA name of Cocamidopropyl Betaine is particularly preferred. Other suitable emulsifiers are ampholytic surfactants. Ampholytic surfactants are understood to be surface-active compounds which, in addition to a $C_{8-18}$ alkyl or acyl group, contain at least one free amino group and at least one —COOH or —$SO_3H$ group in the molecule, and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12-18}$ acyl sarcosine.

Suitable w/o emulsifiers are: (b1) adducts of 2 to 15 moles of ethylene oxide with castor oil and/or hydrogenated castor oil; (b2) partial esters based on linear, branched, unsaturated or saturated $C_{12-22}$ fatty acids, ricinoleic acid or polyricinoleic acid and 12-hydroxystearic acid or poly-12-hydroxystearic acid and glycerol, polyglycerol, pentaerythritol, dipentaerythritol, sugar alcohols (for example sorbitol) and polyglucosides (for example cellulose); (b3) trialkyl phosphates; (b4) wool wax alcohols; (b5) polysiloxane/polyalkyl polyether copolymers and corresponding derivatives; (b6) mixed esters of pentaerythritol, fatty acids, citric acid and fatty alcohol according to DE-PS 11 65 574 and (b7) polyalkylene glycols.

Superfatting agents may be selected from such substances as, for example, polyethoxylated lanolin derivatives, lecithin derivatives, polyol fatty acid esters, monoglycerides and fatty acid alkanolamides, the fatty acid alkanolamides also serving as foam stabilizers. Typical examples of fats are glycerides while suitable waxes are inter alia beeswax, paraffin wax or microwaxes, optionally in combination with hydrophilic waxes, for example, cetostearyl alcohol. Metals salts of fatty acids, for example, magnesium, aluminum and/or zinc stearate, may be used as stabilizers. In the context of the invention, biogenic agents are, for example, plant extracts and vitamin complexes. Suitable preservatives are, for example, phenoxyethanol, formaldehyde solution, parabens, pentanediol or sorbic acid. Suitable pearlescers are, for example, glycol distearic acid esters, such as ethylene glycol distearate, and also fatty acid monoglycol esters. The dyes used may be selected from any of the substances which are permitted and suitable for cosmetic purposes, as listed for example in the publication "Kosmetische Färbemittel" of the Farbstoffkommission der Deutschen Forschungsgemeinschaft, published by Verlag Chemie, Weinheim, 1984, pages 81–106. These dyes are typically used in concentrations of 0.001 to 0.1% by weight, based on the mixture as a whole.

The total content of auxiliaries and additives may be from 1 to 50% by weight and is preferably from 5 to 40% by weight, based on the formulation. The formulations may be produced in known manner, i.e. for example by hot, cold, hot-hot/cold or PIT emulsification. This is a purely mechanical process which does not involve a chemical reaction.

EXAMPLES

The viscosity of various o/w and w/o emulsions using glycoside esters or beeswax as emulsifiers was determined by the Brookfield method (23° C.) in an RVF viscosimeter. Formulations F1 to F7 and F9 correspond to the invention while formulation F8 is intended for comparison. The results are set out in Table 1 (quantities as % by weight). The results show that the glycoside esters according to the invention are as efficient as beeswax in thickening emulsions.

TABLE 1

| Composition | O/w and w/o emulsions | | | | | | | | |
|---|---|---|---|---|---|---|---|---|---|
| | F1 | F2 | F3 | F4 | F5 | F6 | F7 | F8 | F9 |
| Cocoalkyl glucoside dioleate | 1.9 | 7.0 | 3.0 | — | — | — | — | — | — |
| Cocoalkyl glucoside diisostearate | — | — | — | 5.0 | 1.9 | — | — | — | — |
| Cocoalkyl glucoside distearate | — | — | — | — | — | 1.9 | 5.0 | — | 7.0 |
| Beeswax | | | | | | | | 7.0 | |
| LANETTE ® O (Cetearyl Alcohol) | 5.6 | — | — | — | 5.6 | 5.6 | — | 1.0 | 1.0 |
| MYRISTOL ® 312 (Caprylic/Capric Triglyceride) | 16.0 | — | — | — | — | 16.0 | — | — | — |
| Paraffin oil, subl. | — | — | — | — | 16.0 | — | — | — | — |
| LAMEFORM ® TGI (Polyglyceryl-3 Diisostearate) | — | — | — | — | — | — | — | 4.0 | 4.0 |
| MONOMULS ® 90 018 (Glyceryl Oleate) | — | — | — | — | — | — | — | 2.0 | 2.0 |
| CETIOL ® OE (Dicapryl Ether) | — | 20.0 | 20.0 | 20.0 | — | — | 20.0 | — | — |
| CETIOL ® 868 (Octyl Stearate) | — | — | — | — | — | — | — | 21.0 | 21.0 |
| Glycerol, 86% | — | 5.0 | 5.0 | 5.0 | — | — | 5.0 | 5.0 | 5.0 |
| Formalin, 37% | | | | | 0.15 | | | | |
| $M_gSO_4 * 7 H_2O$ | — | 0.5 | 0.5 | 0.5 | — | — | 0.5 | 1.0 | 1.0 |
| Water | | | | ad 100% by weight | | | | | |
| Conductivity [ms] | >20 | 0 | 0 | 0 | >20 | >20 | 0 | 0 | 0 |
| Emulsion type | O/W | W/O | W/O | W/O | O/W | O/W | W/O | W/O | W/O |
| Viscosity [Pas] | 50* | 6# | 3# | 4# | 75* | 400* | 815* | 450* | 450* |

*) Spindle E, 4 r.p.m., with Helipath
) Spindle 5, 10 r.p.m.

What is claimed is:

1. A process for thickening an oil-in-water emulsion comprising adding to the emulsion a thickening agent comprising an alkyl or alkenyl oligoglucoside ester formed by esterifying an alkyl or alkenyl oligoglycoside corresponding to formula I:

$$R^1O-[G]_p \qquad (I)$$

wherein $R^1$ is an alkyl or alkenyl oligoglucoside containing from about 4 to about 22 carbon atoms, G is a sugar unit containing from 5 to 6 carbon atoms, and p is a number having a value of from 1 to about 10, with a fatty acid corresponding to formula II:

$$R^2CO-OH \qquad (II)$$

wherein $R^2CO$ is an aliphatic acyl radical containing from about 6 to about 22 carbon atoms, and up to about 3 double bonds, and a co-thickener selected from the group consisting of a fatty alcohol, a partial glyceride, and mixtures thereof.

2. The process of claim 1 wherein in formula I, $R^1$ is an alkyl radical containing from 8 to 18 carbon atoms, and p is a number having a value of from 1.1 to about 3.0.

3. The process of claim 2 wherein in formula I, p is a number having a value of from 1.2 to about 1.4.

4. The process of claim 1 wherein the fatty acid contains from 16 to 18 carbon atoms.

5. The process of claim 1 wherein the thickening agent is present in the emulsion in an amount of from about 1 to about 10% by weight, based on the weight of the emulsion.

6. The process of claim 5 wherein the thickening agent is present in the emulsion in an amount of from about 2 to about 8% by weight, based on the weight of the emulsion.

7. The process of claim 1 wherein the emulsion comprises a cosmetic composition.

8. The process of claim 1 wherein the emulsion comprises a pharmaceutical composition.

9. The process of claim 1 wherein the thickening agent is an alkyl or alkenyl oligoglucoside monoester.

10. The process of claim 1 wherein the thickening agent is an alkyl or alkenyl oligoglucoside diester.

11. The process of claim 1 wherein the emulsion further comprises an additive selected from the group consisting of a co-emulsifier, a superfatting agent, a biogenic agent, a preservative, a pearlescer, a dye, and mixtures thereof.

12. The process of claim 1 wherein the additive is present in the emulsion in an amount of from about 1 to about 50% by weight, based on the weight of the emulsion.

13. A cosmetic composition comprising from about 1 to about 10% by weight of oil-in-water thickening agent comprising an alkyl or alkenyl oligoglucoside ester formed by esterifying an alkyl or alkenyl oligoglycoside corresponding to formula I:

$$R^1O-[G]_p \qquad (I)$$

wherein $R^1$ is an alkyl or alkenyl oligoglucoside containing from about 4 to about 22 carbon atoms, G is a sugar unit containing from 5 to 6 carbon atoms, and p is a number having a value of from 1 to about 10, with a fatty acid corresponding to formula II:

$$R^2CO-OH \qquad (II)$$

wherein $R^2CO$ is an aliphatic acyl radical containing from about 6 to about 22 carbon atoms, and up to about 3 double bonds, and a co-thickener selected from the group consisting of a fatty alcohol, a partial glyceride, and mixtures thereof.

14. A pharmaceutical composition comprising from about 1 to about 10% by weight of oil-in-water thickening agent comprising an alkyl or alkenyl oligoglucoside ester formed by esterifying an alkyl or alkenyl oligoglycoside corresponding to formula I:

$$R^1O-[G]_p \qquad (I)$$

wherein $R^1$ is an alkyl or alkenyl oligoglucoside containing from about 4 to about 22 carbon atoms, G is a sugar unit containing from 5 to 6 carbon atoms, and p is a number having a value of from 1 to about 10, with a fatty acid corresponding to formula II:

$$R^2CO-OH \qquad (II)$$

wherein $R^2CO$ is an aliphatic acyl radical containing from about 6 to about 22 carbon atoms, and up to about 3 double bonds, and a co-thickener selected from the group consisting of a fatty alcohol, a partial glyceride, and mixtures thereof.

* * * * *